(12) United States Patent
Emerson (10) Patent No.: US 10,967,203 B1
(45) Date of Patent: Apr. 6, 2021

(54) OXYGEN DELIVERY DEVICE

(71) Applicant: Neale Emerson, Venice, FL (US)

(72) Inventor: Neale Emerson, Venice, FL (US)

( * ) Notice: Subject to any disclaimer, the term of this patent is extended or adjusted under 35 U.S.C. 154(b) by 359 days.

(21) Appl. No.: 16/174,390

(22) Filed: Oct. 30, 2018

(51) Int. Cl.
| | |
|---|---|
| *A62B 7/02* | (2006.01) |
| *A61M 16/00* | (2006.01) |
| *A61M 16/06* | (2006.01) |
| *A61M 16/08* | (2006.01) |
| *A62B 9/02* | (2006.01) |
| *A62B 18/02* | (2006.01) |
| *A62B 9/04* | (2006.01) |
| *A61M 16/20* | (2006.01) |

(52) U.S. Cl.
CPC .......... *A62B 7/02* (2013.01); *A61M 16/0075* (2013.01); *A61M 16/06* (2013.01); *A61M 16/0875* (2013.01); *A61M 16/208* (2013.01); *A62B 9/02* (2013.01); *A62B 9/04* (2013.01); *A62B 18/025* (2013.01); *A61M 2202/0208* (2013.01)

(58) Field of Classification Search
CPC ....... A62B 25/00; A62B 7/00–06; A62B 7/14; A62B 9/02–06; A62B 2500/005; A62B 31/00; A62B 18/00–025; A45F 3/14; A45F 2003/146; A45F 2003/142; A45F 3/04; A45F 3/02; A45F 2003/025; B63C 2011/026; A41D 2400/48; A41D 2400/482; A61F 5/37; A61F 5/373; A61F 5/3746; A61F 5/3738; A61F 5/3761; A61M 16/0075; A61M 16/0875; A61M 16/06; A61M 16/208–209; A61M 2202/0208
USPC ............ 128/204.17, 204.18, 204.26, 203.17, 128/203.27, 202.27, 205.11, 205.22, 128/205.25, 200.24, 205.24; 222/3, 154, 222/156; 312/138 R
See application file for complete search history.

(56) References Cited

U.S. PATENT DOCUMENTS

| | | | | |
|---|---|---|---|---|
| 2,063,043 | A | * 12/1936 | McKesson ............ | A61M 16/00 128/204.28 |
| 2,122,897 | A | * 7/1938 | Straw ........................ | F17C 7/00 222/6 |
| 3,800,819 | A | * 4/1974 | McKee ................. | A61M 16/00 137/343 |
| 4,054,133 | A | 10/1977 | Myers | |
| 4,579,114 | A | 4/1986 | Gray | |
| 4,940,049 | A | * 7/1990 | Kirchgeorg ........... | A61M 16/00 128/204.18 |

(Continued)

FOREIGN PATENT DOCUMENTS

WO            0234338         2/2002

*Primary Examiner* — Kendra D Carter
*Assistant Examiner* — Elliot S Ruddie (57) ABSTRACT

The oxygen delivery device is a portable structure. The oxygen delivery device contains a plurality of oxygen canisters. The plurality of oxygen canisters contain oxygen under pressure. The oxygen delivery device stores the plurality of oxygen canisters. The oxygen delivery device dispenses the oxygen contained in the plurality of oxygen canisters. The oxygen delivery device comprises a housing, a distribution apparatus and the plurality of oxygen canisters. The housing contains the plurality of oxygen canisters and the distribution apparatus. The housing: a) stores the plurality of oxygen canisters; and, b) forms a fluidic connection between the plurality of oxygen canisters and the distribution apparatus. The distribution apparatus delivers the oxygen received from the plurality of oxygen canisters for consumption.

12 Claims, 4 Drawing Sheets

(56) References Cited

U.S. PATENT DOCUMENTS

| | | |
|---|---|---|
| 5,121,745 A | 6/1992 | Israel |
| 5,299,565 A | 4/1994 | Brown |
| 5,396,885 A | 3/1995 | Nelson |
| 5,469,842 A | 11/1995 | Flynn |
| 5,613,490 A * | 3/1997 | Mayes ............... A62B 7/02 128/201.27 |
| 5,647,346 A | 7/1997 | Holscher |
| 5,676,135 A | 10/1997 | McClean |
| 6,354,294 B1 | 3/2002 | Villareal, Jr. |
| 7,360,538 B2 | 4/2008 | Flynn |
| 2005/0085799 A1 | 4/2005 | Luria |

* cited by examiner

OXYGEN DELIVERY DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of life-saving equipment including a respiratory apparatus further comprising compressed oxygen. (A62B7/02)

SUMMARY OF INVENTION

The oxygen delivery device is a portable structure. The oxygen delivery device contains a plurality of oxygen canisters. The plurality of oxygen canisters contain oxygen under pressure. The oxygen delivery device stores the plurality of oxygen canisters. The oxygen delivery device dispenses the oxygen contained in the plurality of oxygen canisters. The oxygen delivery device comprises a housing, a distribution apparatus and the plurality of oxygen canisters. The housing contains the plurality of oxygen canisters and the distribution apparatus. The housing: a) stores the plurality of oxygen canisters; and, b) forms a fluidic connection between the plurality of oxygen canisters and the distribution apparatus. The distribution apparatus delivers the oxygen received from the plurality of oxygen canisters for consumption.

These together with additional objects, features and advantages of the oxygen delivery device will be readily apparent to those of ordinary skill in the art upon reading the following detailed description of the presently preferred, but nonetheless illustrative, embodiments when taken in conjunction with the accompanying drawings.

In this respect, before explaining the current embodiments of the oxygen delivery device in detail, it is to be understood that the oxygen delivery device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the oxygen delivery device.

It is therefore important that the claims be regarded as including such equivalent construction insofar as they do not depart from the spirit and scope of the oxygen delivery device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
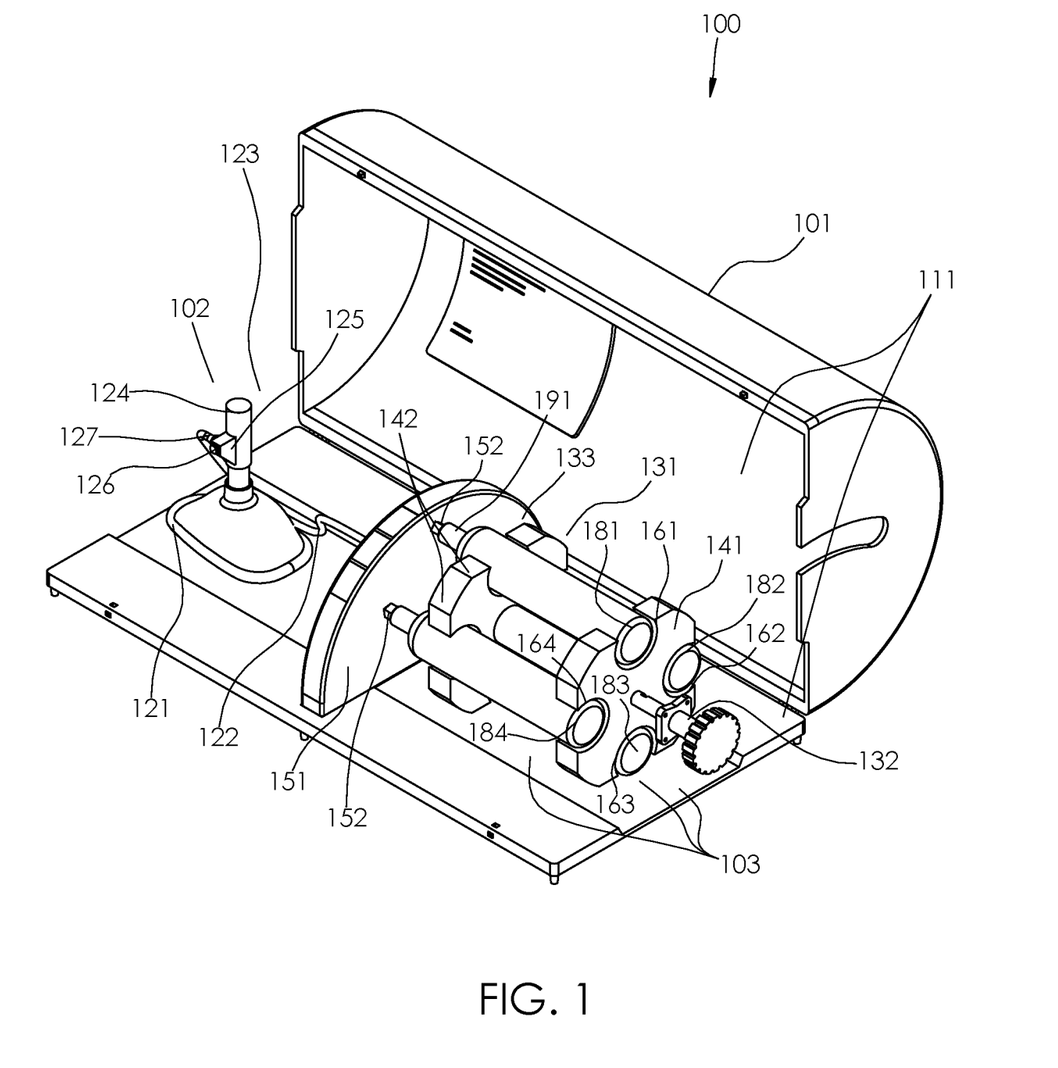
FIG. 1 is a perspective view of an embodiment of the disclosure.
Figure 2:
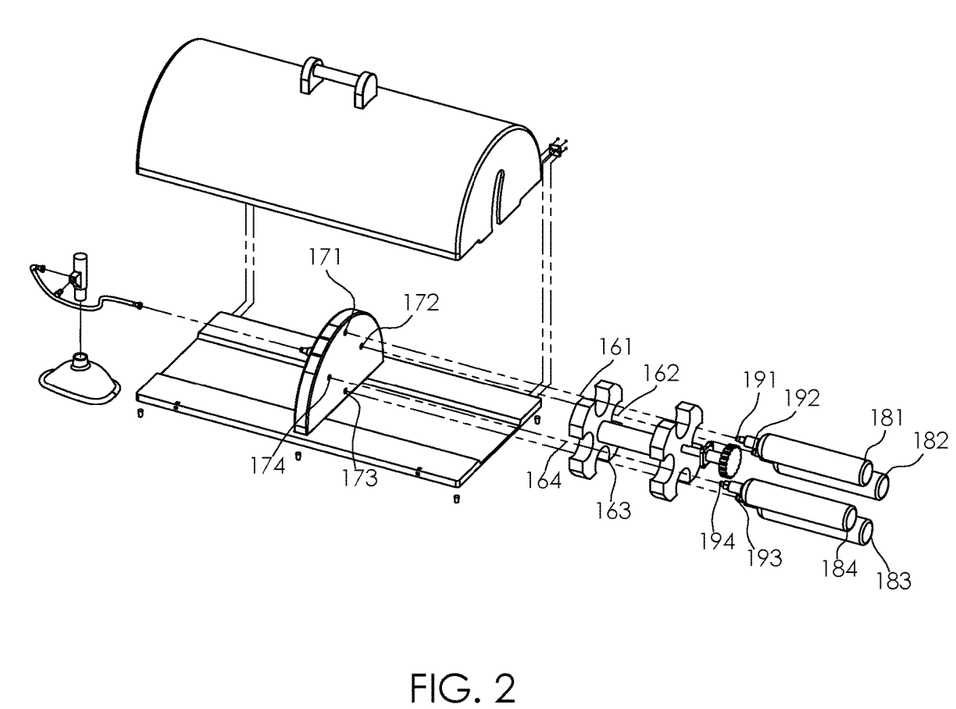
FIG. 2 is an exploded view of an embodiment of the disclosure.
Figure 3:
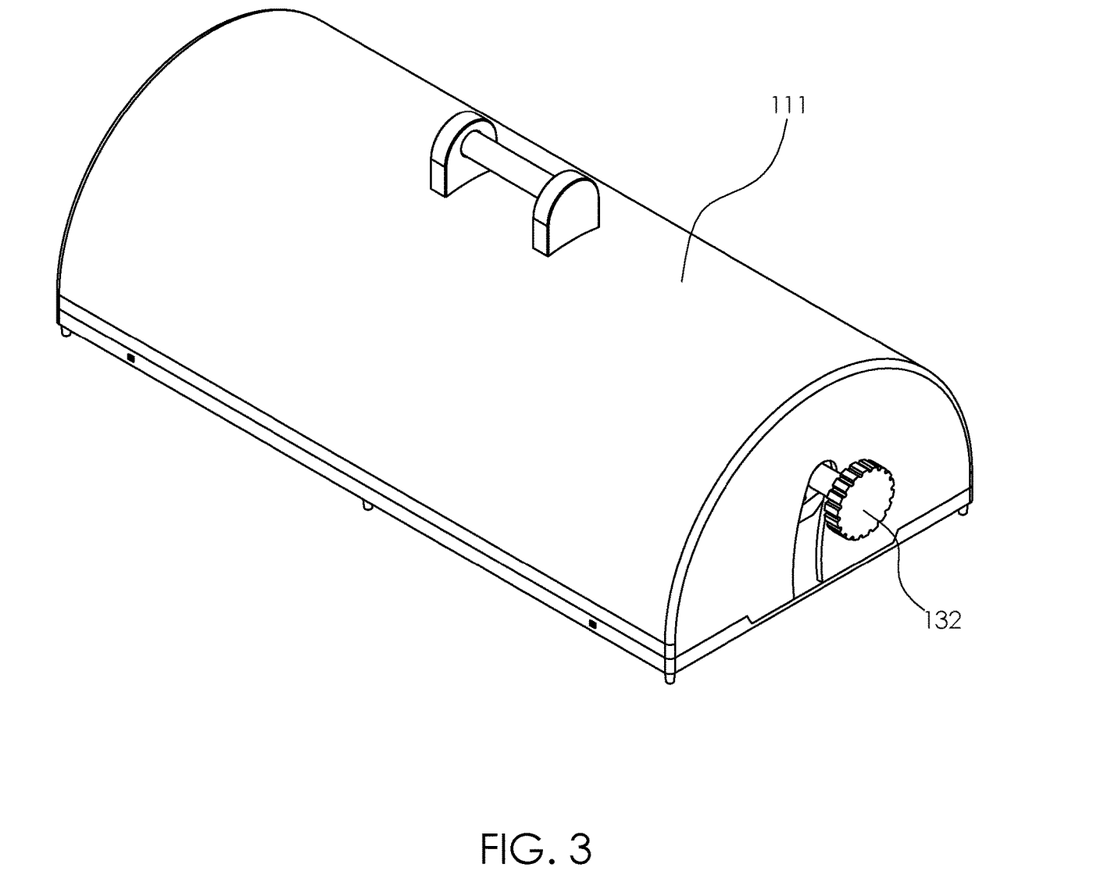
FIG. 3 is a perspective view of an embodiment of the disclosure.
Figure 4:
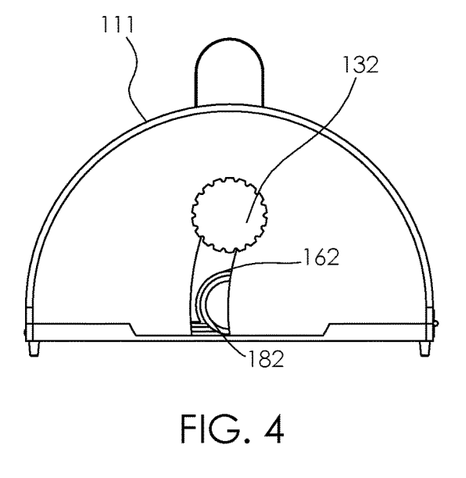
FIG. 4 is a side view of an embodiment of the disclosure.
Figure 5:
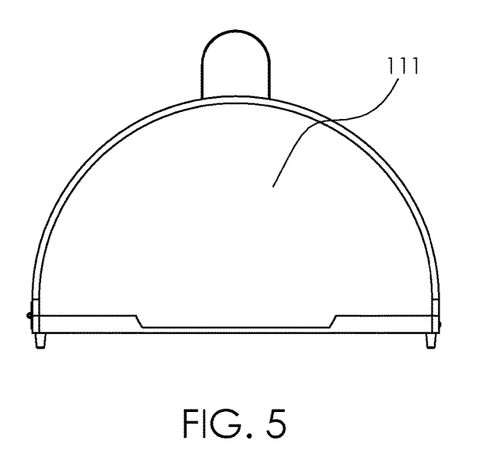
FIG. 5 is a side view of an embodiment of the disclosure.
Figure 6:
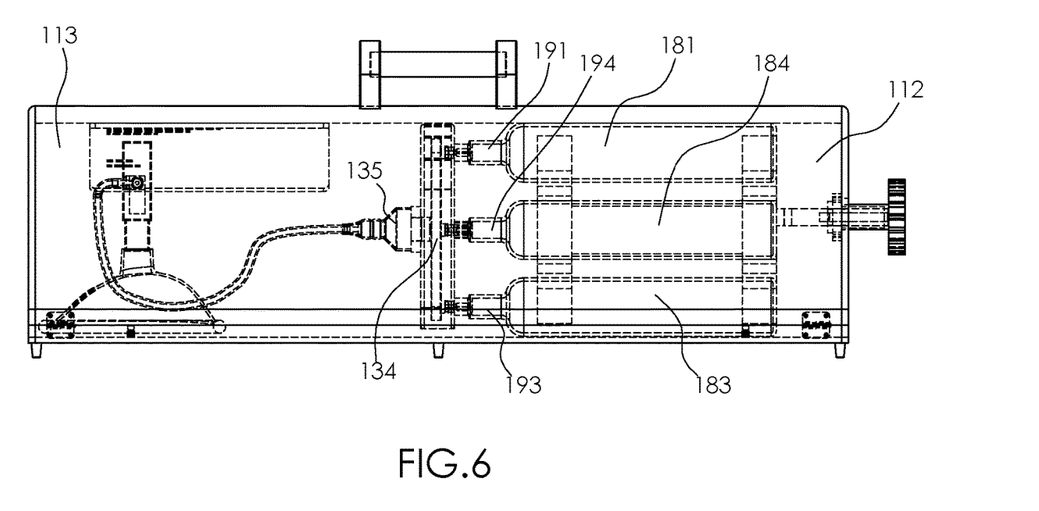
FIG. 6 is a front view of an embodiment of the disclosure.

Detailed reference will now be made to one or more potential embodiments of the disclosure, which are illustrated in FIGS. 1 through 6.

The oxygen delivery device 100 (hereinafter invention) is a portable structure. The invention 100 contains a plurality of oxygen canisters 103. The plurality of oxygen canisters 103 contain oxygen under pressure. The invention 100 stores the plurality of oxygen canisters 103. The invention 100 dispenses the oxygen contained in the plurality of oxygen canisters 103. The invention 100 comprises a housing 101, a distribution apparatus 102 and the plurality of oxygen canisters 103. The housing 101 contains the plurality of oxygen canisters 103 and the distribution apparatus 102. The housing 101: a) stores the plurality of oxygen canisters 103; and, b) forms a fluidic connection between the plurality of oxygen canisters 103 and the distribution apparatus 102. The distribution apparatus 102 delivers the oxygen received from the plurality of oxygen canisters 103 for consumption.

The housing 101 forms the outer structure of the invention 100. The housing 101 contains the plurality of oxygen canisters 103. The housing 101 forms a space for storing the distribution apparatus 102. The housing 101 is a rigid structure. The housing 101 is formed with all apertures and form factors necessary to allow the housing 101 to accommodate the use and operation of the invention 100. The housing 101 comprises a shell 111, a resource chamber 112, and a storage chamber 113.

The shell 111 is a hollow structure. The shell 111 is a rigid structure. The shell 111 has a prism shape. The shell 111 forms the exterior surfaces of the housing 101. The shell 111 is a casing. The shell 111 contains the resource chamber 113 and the storage chamber 112. The shell 111 is formed with all apertures and form factors necessary to allow the shell 111 to accommodate the use and operation of the invention 100. Methods to form a shell 111 suitable for the purposes described in this disclosure are well-known and documented in the mechanical arts.

The storage chamber 113 is a segregated space formed within the hollow interior of the shell 111. The storage chamber 113 forms the space that stores the distribution apparatus 102. The distribution apparatus 102 is stored within the storage chamber such that the distribution apparatus 102 can be removed from the storage chamber 113 during use of the distribution apparatus 102.

The resource chamber 112 is a segregated space formed within the hollow interior of the shell 111. The resource chamber 112 forms the space that stores the plurality of oxygen canisters 103. The resource chamber 112 forms the fluidic connection that transports oxygen in a gas phase from the plurality of oxygen canisters 103 to the distribution apparatus 102. The resource chamber 112 further comprises a canister mount 131, a tension device 132, and a manifold plate 133.

The canister mount 131 is a mechanical structure. The canister mount 131 attaches to the interior surface of the shell 111. Each of the plurality of oxygen canisters 103 removably installs into the canister mount 131. Each of the plurality of oxygen canisters 103 are stored in a fixed position within the canister mount 131. The canister mount 131 comprises a canister block 141 and a plurality of canister racks 142.

The canister block 141 is an openwork prism-shaped structure that forms the basis of the canister mount 131. The canister block 141 forms the framework that receives each of the plurality of oxygen canisters 103. Each of the plurality of canister racks 142 is a negative space that is formed in the canister block 141. Each of the plurality of canister racks 142 is sized to receive a canister selected from the plurality of oxygen canisters 103. Each of the plurality of oxygen canisters 103 are stored within a rack selected from the plurality of canister racks 142.

The tension device 132 is a mechanical device. The tension device 132 is a spring-loaded device. The tension device 132 applies a force against each of the plurality of oxygen canisters 103. The force applied by the tension device 132 to the plurality of oxygen canisters 103 ensures that the canister valve of each of the plurality of oxygen canisters 103 is properly seated in the manifold plate 133 such that the manifold plate 133 will receive the oxygen in a gas phase contained within each of the plurality of oxygen canisters 103.

The manifold plate 133 is a fluidic connection that: a) receives the oxygen in a gas phase from each of the plurality of oxygen canisters 103; b) aggregates the oxygen in a gas phase received from the plurality of oxygen canisters 103 through a fluidic network 134; and, c) transports and releases the aggregated oxygen in a gas phase through the outlet fitting 135. The manifold plate 133 comprises a manifold block 151, a plurality of inlet fittings 152, a fluidic network 134, and an outlet fitting 135.

The fluidic network 134 comprises a network of fluidic connections that aggregate the received multiple oxygen flows into a single flow of the oxygen in a gas phase which discharges through the outlet fitting 135. The outlet fitting 135 is a fitting. The outlet fitting 135 discharges the oxygen in a gas phase that is received by the manifold plate 133 to the hose 122 of the distribution apparatus 102.

The manifold block 151 is a solid prism-shaped structure. The manifold block 151 forms a barrier that segregates the resource chamber 112 from the storage chamber 113. The fluidic network 134 is formed within the manifold block 151. The outlet fitting 135 attaches to the fluidic network 134 formed within the manifold block 151.

Each of the plurality of inlet fittings 152 is a fitting adapted to connect to the canister valve of a canister selected from the plurality of oxygen canisters 103. Each of the plurality of inlet fittings 152 forms a fluidic connection between the canister valve of a canister selected from the plurality of oxygen canisters 103 and the fluidic network 134 of the manifold plate 133.

The plurality of canister racks 142 further comprises a first canister rack 161, a second canister rack 162, a third canister rack 163, and a fourth canister rack 164. The first canister rack 161, the second canister rack 162, the third canister rack 163, and the fourth canister rack 164 are identical.

The plurality of inlet fittings 152 further comprises a first inlet fitting 171, a second inlet fitting 172, a third inlet fitting 173, and a fourth inlet fitting 174. The first inlet fitting 171, the second inlet fitting 172, the third inlet fitting 173, and the fourth inlet fitting 174 are identical.

The distribution apparatus 102 is a fluid transport structure. The distribution apparatus 102 delivers oxygen in a gas phase from the resource chamber 112 to a point of consumption. The distribution apparatus 102 comprises a mask 121, a hose 122, and an oxygen connector 123.

The mask 121 physically delivers oxygen in a gas phase directly to the point of consumption. The mask 121 is a structure that encloses the point of consumption. The mask 121 forms a fluid impermeable seal around a surface formed at the point of consumption. The hose 122 is a fluid transport structure. The hose 122 is a commercially available flexible tubing. The hose 122 attaches to the outlet fitting 135 of the manifold plate 133 such that the hose 122 draws oxygen in a gas phase directly from the manifold plate 133. The oxygen connector 123 is a fluid transport structure.

The oxygen connector 123 forms a fluidic connection between the mask 121 and the hose 122. The oxygen connector 123 is a rigid structure. The oxygen connector 123 is a hollow structure. The oxygen connector 123 comprises a bellows connection 124 and a feed/exhaust structure 125.

The bellows connection 124 is a tube that inserts into the mask 121. The bellows connection 124 is configured for use emergency use. The end of the bellows connection 124 that is distal from the mask 121 is normally closed. The end of the bellows connection 124 that is distal from the mask 121 can open to the atmosphere. The bellows connection 124 is sized to receive a bellows. The bellows is a manually operated pump used by emergency services personnel. The bellows forces fresh atmospheric gas to the point of consumption in an emergency situation.

The feed/exhaust structure 125 is a mechanical structure that: a) feeds the oxygen in a gas phase to the consumption point; and, b) discharges exhalation gases generated at the consumption point. The feed/exhaust structure 125 is a tubular structure. The feed/exhaust structure 125 branches off of the bellows connection 124. The feed/exhaust structure 125 further comprises an exhaust port 126 and a feed valve 127.

The exhaust port 126 is a port through which the exhaust gases are discharged from the feed/exhaust structure 125. The exhaust port 126 is a check valve that mounts on the end of the tubular structure of the feed/exhaust structure 125 that is distal from the mask 121. The exhaust port 126 opens under exhalation pressure to release the exhaled gases.

The feed valve 127 is a port through which the oxygen in a gas phase feeds into the feed/exhaust structure 125 for transport to the mask 121. The feed valve 127 is a check valve that mounts through the lateral face of the tubular structure of the feed/exhaust structure 125. The oxygen in a gas phase flows through the feed valve 127 and the feed/exhaust structure 125 to the mask 121. The feed valve 127 opens in response to an inhalation vacuum to allow the flow of oxygen in a gas phase into the feed/exhaust structure 125.

Each of the plurality of oxygen canisters 103 is a rigid structure that contains oxygen as a pressurized fluid. Each of the plurality of oxygen canisters 103 is stored within the resource chamber 112 of the housing 101. Each of the plurality of oxygen canisters 103 has a canister valve that releases the oxygen in a gas phase from the selected canister. Each of the plurality of oxygen canisters 103 releases the stored oxygen in a gas phase through the resource chamber 112 of the housing 101 to the distribution apparatus 102 where it is distributed for consumption.

The plurality of oxygen canisters 103 comprises a first oxygen canister 181, a second oxygen canister 182, a third oxygen canister 183, and a fourth oxygen canister 184. The first oxygen canister 181, the second oxygen canister 182, the third oxygen canister 183, and the fourth oxygen canister 184 are identical. The first oxygen canister 181 comprises a first oxygen canister valve 191. The second oxygen canister 182 comprises a second oxygen canister valve 192. The third oxygen canister 183 comprises a third oxygen canister valve 193. The fourth oxygen canister 184 comprises a fourth oxygen canister valve 194. The first oxygen canister valve 191, the second oxygen canister valve 192, the third oxygen canister valve 193, and the fourth oxygen canister valve 194 are identical.

The following three paragraphs describe the assembly of the invention 100.

The first canister rack 161 of the plurality of canister racks 142 stores the first oxygen canister 181 of the plurality of oxygen canisters 103. The second canister rack 162 of the plurality of canister racks 142 stores the second oxygen canister 182 of the plurality of oxygen canisters 103. The third canister rack 163 of the plurality of canister racks 142 stores the third oxygen canister 183 of the plurality of oxygen canisters 103. The fourth canister rack 164 of the plurality of canister racks 142 stores the fourth oxygen canister 184 of the plurality of oxygen canisters 103.

The first oxygen canister valve 191 of the first oxygen canister 181 inserts into the first inlet fitting 171 of the plurality of inlet fittings 152. The second oxygen canister valve 192 of the second oxygen canister 182 inserts into the second inlet fitting 172 of the plurality of inlet fittings 152. The third oxygen canister valve 193 of the third oxygen canister 183 inserts into the third inlet fitting 173 of the plurality of inlet fittings 152. The fourth oxygen canister valve 194 of the fourth oxygen canister 184 inserts into the fourth inlet fitting 174 of the plurality of inlet fittings 152.

The hose 122 forms a fluidic connection between the outlet fitting 135 of the manifold plate 133 and the feed valve 127 of the feed/exhaust structure 125 of the oxygen connector 123. The bellows connection 124 of the oxygen connector 123 attaches to the mask 121.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Ball Valve: As used in this disclosure, a ball valve is a type of commercially available check valve.

Canister: As used in this disclosure, a canister is a containment vessel configured for use in storing a fluid under pressure.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Chamber: As used in this disclosure, a chamber is an enclosed or enclosable negative space dedicated to a purpose.

Check Valve: As used in this disclosure, a check valve is a valve that permits the flow of fluid or gas in a single direction. Within selected potential embodiments of this disclosure, the check valve is a commercially available product that is selected from the group consisting of a ball valve and a Tesla valve.

Compression Spring: As used in this disclosure, a compression spring is a spring that resists forces attempting to compress the spring in the direction of the center axis of the spring. The compression spring will return to its original position when the compressive force is removed.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. Specifically, the sum of the surface areas of two ends of the prism-shaped object that forms the disk is greater than the surface area of the lateral face of the prism-shaped object that forms the disk. In this disclosure, the ends of the prism-shaped structure that forms the disk are referred to as the faces of the disk.

Fitting: As used in this disclosure, a fitting is a component that is attached to a first object. The fitting is used to forming a fluidic connection between the first object and a second object.

Fluid: As used in this disclosure, a fluid refers to a state of matter wherein the matter is capable of flow and takes the shape of a container it is placed within. The term fluid commonly refers to a liquid or a gas.

Fluidic Connection: As used in this disclosure, a fluidic connection refers to a tubular structure that transports a fluid from a first object to a second object. Methods to design and use a fluidic connection are well-known and documented in the mechanical, chemical, and plumbing arts.

Form Factor: As used in this disclosure, the term form factor refers to the size and shape of an object.

Gas: As used in this disclosure, a gas refers to a state (phase) of matter that is fluid and that fills the volume of the structure that contains it. Stated differently, the volume of a gas always equals the volume of its container.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Hose: As used in this disclosure, a hose is a flexible hollow prism-shaped device used for transporting liquids and gases. When referring to a hose in this disclosure, the terms inner diameter and outer diameter are used as they would be used by those skilled in the plumbing arts.

Housing: As used in this disclosure, a housing is a rigid casing that encloses and protects one or more devices.

Inner Dimension: As used in this disclosure, the term inner dimension describes the span from a first inside or interior surface of a container to a second inside or interior surface of a container. The term is used in much the same way that a plumber would refer to the inner diameter of a pipe.

Liquid: As used in this disclosure, a liquid refers to a state (phase) of matter that is fluid and that maintains, for a given pressure, a fixed volume that is independent of the volume of the container.

Manifold: As used in this disclosure, a manifold is a pipe or chamber having several ports through which liquid or gas is gathered or distributed.

Negative Space: As used in this disclosure, negative space is a method of defining an object through the use of open or empty space as the definition of the object itself, or, through the use of open or empty space to describe the boundaries of an object.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Outer Dimension: As used in this disclosure, the term outer dimension describes the span from a first exterior or outer surface of a tube or container to a second exterior or outer surface of a tube or container. The term is used in much the same way that a plumber would refer to the outer diameter of a pipe.

Oxygen: As used in this disclosure, oxygen (CAS 7782-44-7) refers to the element with atomic number 8 in the periodic table. The chemical abbreviation for oxygen is 02. Oxygen is a diatomic element.

Perimeter: As used in this disclosure, a perimeter is one or more curved or straight lines that bounds an enclosed area on a plane or surface. The perimeter of a circle is commonly referred to as a circumference.

Plate: As used in this disclosure, a plate is a smooth, flat and semi-rigid or rigid structure that has at least one dimension that: a) is of uniform thickness; and b) that appears thin relative to the other dimensions of the object. Plates often have a rectangular appearance. Plates often have a disk-like structure. The face of the plate is a surface of the plate selected from the group consisting of: a) the surface of the plate with the greatest surface area; b) the surface of the plate that is distal from the surface of the plate with the greatest surface area. The edges of the plate comprise the surfaces of the plate that would not be considered faces as defined above. As defined in this disclosure, plates may be made of any material, but are commonly made of metal, plastic, and wood. When made of wood, a plate is often referred to as a board or a plank.

Pressure: As used in this disclosure, pressure refers to a measure of force per unit area.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Rigid Structure: As used in this disclosure, a rigid structure is a solid structure formed from an inelastic material that resists changes in shape. A rigid structure will permanently deform as it fails under a force.

Spring: As used in this disclosure, a spring is a device that is used to store mechanical energy. This mechanical energy will often be stored by: 1) deforming an elastomeric material that is used to make the device; 2) the application of a torque to a semi-rigid structure; or 3) a combination of the previous two items.

Tube: As used in this disclosure, a tube is a hollow prism-shaped device formed with two open ends. The tube is used for transporting liquids and gases. The line that connects the center of the first congruent face of the prism to the center of the second congruent face of the prism is referred to as the center axis of the tube or the centerline of the tube. When two tubes share the same centerline they are said to be aligned. When the centerlines of two tubes are perpendicular to each other, the tubes are said to be perpendicular to each other. In this disclosure, the terms inner dimensions of a tube and outer dimensions of a tube are used as they would be used by those skilled in the plumbing arts.

Valve: As used in this disclosure, a valve is a device that is used to control the flow of a fluid (gas or liquid) through a pipe.

With respect to the above description, it is to be realized that the optimum dimensional relationship for the various components of the invention described above and in FIGS.

1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A respiratory apparatus comprising:
   a housing, a distribution apparatus and a plurality of oxygen canisters;
   wherein the housing contains the plurality of oxygen canisters and the distribution apparatus;
   wherein the respiratory apparatus is a portable structure;
   wherein the respiratory apparatus contains the plurality of oxygen canisters;
   wherein the plurality of oxygen canisters contain oxygen under pressure;
   wherein the respiratory apparatus stores the plurality of oxygen canisters;
   wherein the respiratory apparatus dispenses the oxygen contained in the plurality of oxygen canisters;
   wherein each of the plurality of oxygen canisters further comprises a canister valve;
   wherein the housing forms the outer structure of the respiratory apparatus;
   wherein the housing forms a fluidic connection between the plurality of oxygen canisters and the distribution apparatus;
   wherein the housing comprises a shell, a resource chamber, and a storage chamber;
   wherein the resource chamber and the storage chamber are contained within the shell;
   wherein the resource chamber further comprises a canister mount, a tension device, and a manifold plate;
   wherein the resource chamber contains the canister mount, the tension device, and the manifold plate;
   wherein the canister mount comprises a canister block and a plurality of canister racks;
   wherein the plurality of canister racks are formed in the canister block;
   wherein the canister block is an openwork prism-shaped structure that forms the basis of the canister mount;
   wherein the canister block forms the framework that receives each of the plurality of oxygen canisters;
   wherein each of the plurality of canister racks is a negative space formed in the canister block;
   wherein each of the plurality of canister racks is sized to receive a canister selected from the plurality of oxygen canisters
   wherein the shell is a hollow structure;
   wherein the shell is a rigid structure;
   wherein the shell has a prism shape;
   wherein the shell forms the exterior surfaces of the housing
   wherein the storage chamber is a segregated space formed within the hollow interior of the shell;
   wherein the storage chamber forms the space that stores the distribution apparatus;
   wherein the distribution apparatus is stored within the storage chamber such that the distribution apparatus is removable from the storage chamber during use of the distribution apparatus;
   wherein the resource chamber is a segregated space formed within the hollow interior of the shell; wherein the resource chamber forms the space that stores the plurality of oxygen canisters;
   wherein the resource chamber forms the fluidic connection that transports oxygen in a gas phase from the plurality of oxygen canisters to the distribution apparatus.

2. The respiratory apparatus according to claim 1 wherein the distribution apparatus is a fluid transport structure; wherein the distribution apparatus delivers oxygen in the gas phase from the resource chamber to a point of consumption.

3. The respiratory apparatus according to claim 2 wherein the canister mount is a mechanical structure;
   wherein the canister mount attaches to the interior surface of the shell;
   wherein each of the plurality of oxygen canisters removably installs into the canister mount;
   wherein each of the plurality of oxygen canisters are stored in a fixed position within the canister mount.

4. The respiratory apparatus according to claim 3
   wherein the tension device is a mechanical device;
   wherein the tension device is a spring-loaded device;
   wherein the tension device applies a force against each of the plurality of oxygen canisters;
   wherein the tension device ensures that the canister valve of each of the plurality of oxygen canisters is properly seated in the manifold plate.

5. The respiratory apparatus according to claim 4
   wherein the manifold plate receives the oxygen in the gas phase from each of the plurality of oxygen canisters;
   wherein the manifold plate aggregates the oxygen in the gas phase received from the plurality of oxygen canisters through a fluidic network.

6. The respiratory apparatus according to claim 5
   wherein the manifold plate comprises a manifold block, a plurality of inlet fittings, the fluidic network, and an outlet fitting;
   wherein the manifold block, the plurality of inlet fittings, the fluidic network, and the outlet fitting are fluidically interconnected;
   wherein the fluidic network aggregate the received multiple oxygen flows into a single flow of the oxygen in the gas phase which discharges through the outlet fitting; wherein the outlet fitting attaches to the fluidic network formed within the manifold block; wherein the outlet fitting discharges the oxygen in the gas phase that is received by the manifold plate to the distribution apparatus
   wherein the manifold block is a solid prism-shaped structure;
   wherein the manifold block forms a barrier that segregates the resource chamber from the storage chamber;
   wherein the fluidic network is formed within the manifold block;
   wherein each of the plurality of inlet fittings is a fitting adapted to connect to the canister valve of a canister selected from the plurality of oxygen canisters;
   wherein each of the plurality of inlet fittings forms a fluidic connection between the canister valve of a canister selected from the plurality of oxygen canisters and the fluidic network of the manifold plate.

7. The respiratory apparatus according to claim 6
wherein the distribution apparatus comprises a mask, a hose, and an oxygen connector;
wherein the oxygen connector forms a fluidic connection between the mask and the hose;
wherein the mask physically delivers oxygen in the gas phase directly to the point of consumption; wherein the hose, is a flexible tubing: wherein the hose attaches to the outlet fitting of the manifold plate such that the hose draws oxygen in the gas phase directly from the manifold plate
wherein the oxygen connector is a fluid transport structure;
wherein the oxygen connector is a rigid structure;
wherein the oxygen connector is a hollow structure.

8. The respiratory apparatus according to claim 7
wherein the oxygen connector comprises a bellows connection and a feed/exhaust structure;
wherein the feed/exhaust structure branches off of the bellows connection;
wherein the bellows connection is a tube;
wherein the bellows connection inserts in the mask;
wherein the end of the bellows connection that is distal from the mask opens and closes to the atmosphere;
wherein the feed/exhaust structure is a mechanical structure that feeds the oxygen in the gas phase to the consumption point
wherein the feed/exhaust structure discharges exhalation gases generated at the consumption point;
wherein the feed/exhaust structure is a tubular structure.

9. The respiratory apparatus according to claim 8
wherein the feed/exhaust structure further comprises an exhaust port and a feed valve;
wherein the exhaust port is a check valve that mounts on the end of the tubular structure of the feed/exhaust structure that is distal from the mask;
wherein the exhaust port opens under pressure;
wherein the feed valve is a check valve that mounts through the lateral face of the tubular structure of the feed/exhaust structure;
wherein the feed valve opens under a vacuum.

10. The respiratory apparatus according to claim 9
wherein the plurality of canister racks further comprises a first canister rack, a second canister rack, a third canister rack, and a fourth canister rack;
wherein the first canister rack, the second canister rack, the third canister rack, and the fourth canister rack are identical;
wherein the plurality of inlet fittings further comprises a first inlet fitting, a second inlet fitting, a third inlet fitting, and a fourth inlet fitting;
wherein the first inlet fitting, the second inlet fitting, the third inlet fitting, and the fourth inlet fitting are identical.

11. The respiratory apparatus according to claim 10
wherein each of the plurality of oxygen canisters is a rigid structure that contains oxygen as a pressurized fluid;
wherein the plurality of oxygen canisters comprises a first oxygen canister, a second oxygen canister, a third oxygen canister, and a fourth oxygen canister;
wherein the first oxygen canister, the second oxygen canister, the third oxygen canister, and the fourth oxygen canister are identical;
wherein the first oxygen canister comprises a first oxygen canister valve;
wherein the second oxygen canister comprises a second oxygen canister valve;
wherein the third oxygen canister comprises a third oxygen canister valve;
wherein the fourth oxygen canister comprises a fourth oxygen canister valve;
wherein the first oxygen canister valve, the second oxygen canister valve, the third oxygen canister valve, and the fourth oxygen canister valve are identical.

12. The respiratory apparatus according to claim 11
wherein the first canister rack of the plurality of canister racks stores the first oxygen canister of the plurality of oxygen canisters;
wherein the second canister rack of the plurality of canister racks stores the second oxygen canister of the plurality of oxygen canisters;
wherein the third canister rack of the plurality of canister racks stores the third oxygen canister of the plurality of oxygen canisters;
wherein the fourth canister rack of the plurality of canister racks stores the fourth oxygen canister of the plurality of oxygen canisters;
wherein the first oxygen canister valve of the first oxygen canister inserts into the first inlet fitting of the plurality of inlet fittings;
wherein the second oxygen canister valve of the second oxygen canister inserts into the second inlet fitting of the plurality of inlet fittings;
wherein the third oxygen canister valve of the third oxygen canister inserts into the third inlet fitting of the plurality of inlet fittings;
wherein the fourth oxygen canister valve of the fourth oxygen canister inserts into the fourth inlet fitting of the plurality of inlet fittings;
wherein the hose forms a fluidic connection between the outlet fitting of the manifold plate and the feed valve of the feed/exhaust structure of the oxygen connector;
wherein the bellows connection of the oxygen connector attaches to the mask.

* * * * *